United States Patent
Holroyd et al.

(10) Patent No.: US 12,336,927 B2
(45) Date of Patent: Jun. 24, 2025

(54) OUTLET VALVE FOR AN OSTOMY APPLIANCE

(71) Applicant: CONVATEC LIMITED, Flintshire (GB)

(72) Inventors: Simon Holroyd, London (GB); Dominic Baker, London (GB); Stefan Taal, London (GB); Graham Lacy, London (GB)

(73) Assignee: CONVATEC LIMITED, Flintshire (GB)

( * ) Notice: Subject to any disclaimer, the term of this patent is extended or adjusted under 35 U.S.C. 154(b) by 1019 days.

(21) Appl. No.: 17/178,539

(22) Filed: Feb. 18, 2021

(65) Prior Publication Data

US 2021/0251797 A1     Aug. 19, 2021

Related U.S. Application Data

(63) Continuation of application No. PCT/GB2021/050393, filed on Feb. 18, 2021.

(30) Foreign Application Priority Data

Feb. 19, 2020   (GB) ..................................... 2002317
Feb. 19, 2020   (GB) ..................................... 2002318
Feb. 19, 2020   (GB) ..................................... 2002319

(51) Int. Cl.
*A61F 5/44*          (2006.01)
*A61F 5/445*         (2006.01)

(52) U.S. Cl.
CPC ............ *A61F 5/4405* (2013.01); *A61F 5/445* (2013.01)

(58) Field of Classification Search
CPC .............................. A61F 5/4405; A61F 5/445
See application file for complete search history.

(56) References Cited

U.S. PATENT DOCUMENTS 4,280,498 A     7/1981   Jensen
4,603,837 A     8/1986   Steer
(Continued)

FOREIGN PATENT DOCUMENTS

CN          1115729 A       1/1996
CN          1242827 A       1/2000
(Continued)

OTHER PUBLICATIONS

International Search Report; European Patent Office; International Application No. PCT/GB2021/050393; Jul. 2, 2021; 6 pages.
(Continued)

*Primary Examiner* — Susan S Su
*Assistant Examiner* — Erin A Kim
(74) *Attorney, Agent, or Firm* — TAFT STETTINIUS HOLLISTER LLP; Ryan O. White; Derek B. Lavender

(57) ABSTRACT

An outlet valve for an ostomy appliance comprises an axle defining a hollow bore for receiving a liquid output from the ostomy appliance. The axle comprises a curved lateral wall. An outlet element comprises a cap arranged concentrically with the axle and an outlet tube affixed to the cap. A valve opening is defined in the curved lateral wall. The cap is rotatable around the axle to move from a closed configuration in which the valve opening is not in liquid communication with the outlet tube to an open configuration in which the valve opening is in liquid communication with the outlet tube. The outlet valve further comprises an outlet element seal configured to provide: sealing between the cap and the axle around a circumference of the axle; and sealing between the valve opening and the intake opening when the outlet element is in the closed configuration.

7 Claims, 11 Drawing Sheets

(56) References Cited

U.S. PATENT DOCUMENTS

| | | | | |
|---|---|---|---|---|
| 5,902,294 A | * | 5/1999 | Edwards | A61F 5/4405 604/350 |
| 6,021,928 A | * | 2/2000 | Falconer | A61F 5/4405 222/554 |
| 2012/0259300 A1 | * | 10/2012 | Bjerregaard | F16K 5/0407 604/327 |
| 2015/0059901 A1 | * | 3/2015 | Jin | A61F 5/4405 137/798 |
| 2015/0190272 A1 | * | 7/2015 | Chang | A61F 5/445 604/335 |

FOREIGN PATENT DOCUMENTS

| | | | | |
|---|---|---|---|---|
| CN | 1780999 | A | | 5/2006 |
| CN | 101396309 | A | | 1/2009 |
| CN | 102481445 | A | | 5/2012 |
| CN | 102979627 | A | | 3/2013 |
| DE | 69818903 | T2 | | 9/2004 |
| EP | 0680296 | | | 9/1993 |
| EP | 0680296 | B1 | | 5/1997 |
| EP | 2891475 | A1 | | 7/2015 |
| EP | 3181101 | A1 | | 6/2017 |
| GB | 2118685 | A | * 11/1983 | A61F 5/4405 |
| TW | 384353 | B | | 3/2000 |
| WO | 9317642 | A1 | | 9/1993 |
| WO | 2017102959 | A1 | | 6/2017 |

OTHER PUBLICATIONS

Written Opinion of the International Searching Authority; European Patent Office; International Application No. PCT/GB2021/050393; Jul. 2, 2021; 13 pages.

IPO Search Report Under Section 17, Priority Application No. GB2002317.2; Dated: Jul. 16, 2020; pp. 1-3.

IPO Search Report Under Section 17, Priority Application No. GB2002318.0; Dated: Jul. 16, 2020; pp. 1-3.

IPO Search Report Under Section 17, Priority Application No. GB2002319.8; Dated: Jul. 16, 2020; pp. 1-3.

* cited by examiner

OUTLET VALVE FOR AN OSTOMY APPLIANCE

CROSS-REFERENCE TO RELATED APPLICATIONS

This application is a continuation of International Application No. PCT/GB2021/050393 filed Feb. 18, 2021 and claims the priority of foreign Application Nos. GB2002317.2, GB2002318.0, and GB2002319.8, each filed Feb. 19, 2020. The disclosures of which are hereby incorporated herein in their entirety.

TECHNICAL FIELD

The present disclosure relates to an outlet valve an ostomy appliance, particularly for a drainage of a liquid output from an ostomy bag.

BACKGROUND OF THE DISCLOSURE

An ostomy appliance may be provided with an outlet valve for draining liquid from the bag of the ostomy appliance, either for direct disposal of the liquid or via an additional appliance such as a drain bag which may be attached to the outlet valve in use. There are many forms of ostomy appliance which try to provide an easily drainable appliance.

EP0680296 discloses an outlet valve consisting of a base member and at least one movable means which together form a discharge tube or hose member, a stop valve and a closing valve, said movable means being rotatably and/or linearly displaceable and by means of which the valve system can be set in three positions, a first position in which both the stop valve and the closing valve are open, a second position in which the stop valve is closed and the closing valve is open, and a third position in which both valves are closed. A collection bag provided with an outlet valve as stated above.

U.S. Pat. No. 4,280,498 discloses a drain assembly for a urostomy pouch or other similar collection device for permitting continuous overnight draining of the pouch into a suitable receptacle. The assembly includes a body member adapted to be secured to a pouch at the lower end thereof and defining a path for the outflow of the fluid contents of the pouch, a rotary valve member for selectively opening and closing the flow passage, and a drainage tube equipped with a coupler for releasably engaging a stem portion of the valve member.

There remains a need for ostomy appliances with enhanced usability for ostomates, particularly in the area of ease of use, particularly when connecting the outlet valve to an additional appliance, for example a drain bag.

SUMMARY OF THE DISCLOSURE

In this specification, the term "stomal output" refers to any gases or fluids or solids produced by an ostomate that may be secreted from the stoma or that exit the stoma.

In this specification, the term "stoma" refers to an opening in the body. Generally, the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy appliance disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

Beneficially, the ostomy appliances of the present disclosure may permit an ostomate to increase the period of use of each ostomy appliance compared to prior art appliances. This may be achieved by providing means for draining the cavity of stomal output reliably and hygienically so as to increase an ostomate's confidence in reusing the ostomy appliance compared to some prior art appliances. Since the ostomate may be inclined to use each ostomy appliance of the present disclosure for longer, the total number of ostomy appliances used by the ostomate in a given time period may be reduced. This may produce an environmental benefit in reducing the amount of environmental waste produced.

In this specification locations and orientations of features may be described with reference to the ostomy appliance being "in use", "orientated as it would be in use" or similar. Such terms refer to the intended orientation of the ostomy appliance when it is adhered to a body of an ostomate with the ostomate in a standing position, irrespective of whether the ostomy appliance is currently performing such a use or the actual position of the ostomate. The terms "upper" and "lower" and related terms refer to the relative position of a part or portion of the ostomy appliance when orientated as it would be in use. For example, an apex of the ostomy appliance may be referred to as an "lower" apex in use of the ostomy appliance. In such an example, said apex will be intended to be the lowermost apex (in the vertical direction) of the ostomy appliance when attached to the body of a standing ostomate. However, the reader skilled in the art will appreciate that before attachment to the ostomate said apex may not always be the lowermost apex and in addition when attached the apex may not always be the lowermost apex if the ostomate adopts a non-standing position, for example lying down.

In this specification the term "front" refers to the relative position of a part or portion of the ostomy appliance with reference to the body of an ostomate when the ostomy appliance is attached to the body. "Front" refers to a position relatively further away from the body of the ostomate than a comparative position that is relatively closer to the body. Similarly, "back" refers to a position relatively closer to the body of the ostomate than a comparative position that is "front".

In this specification, the terms "inner" and "outer" with reference to parts of the outlet valve refer to the relative position of a part or portion of the ostomy appliance with reference to the axis of rotation of the outlet element, a relatively "inner" part being closer to the axis of rotation than a relatively "outer" part.

In this specification, the term "affixed" is used to refer to a connection in which the component in question cannot be removed during normal use of the outlet valve or without damaging the component.

The present disclosure provides an outlet valve for an ostomy appliance comprising:
- an axle defining a hollow bore for receiving a liquid output from the ostomy appliance, the axle comprising a curved lateral wall and an axle end wall arranged across the hollow bore; and
- an outlet element comprising a cap arranged concentrically with the axle and an outlet tube affixed to the cap;

wherein:
- a valve opening is defined in a portion of the axle end wall; and
- the cap is rotatable around the axle to move the outlet element from a closed configuration in which the valve opening is not in liquid communication with the outlet tube to an open configuration in which the valve opening is in liquid communication with the outlet tube.

The cap may comprise an inner cap end portion arranged to overlie the axle end wall and the inner cap end portion may comprise an intake opening being arranged to be rotatable into a position in which the intake opening at least partially aligns with the valve opening such that the outlet element is in the open configuration, wherein, the intake opening may have an arcuate shape aligned with a circumference around the axis of rotation of the cap.

Thus, the user is able to control the flow rate of fluid through the valve by rotating the cap, and the valve is also configurable so that multiple cap positions correspond to the open configuration.

The cap may comprise an inner cap end portion arranged to overlie the axle end wall and the inner cap end portion may comprise an intake opening being arranged to be rotatable into a position in which the intake opening at least partially aligns with the valve opening such that the outlet element is in the open configuration, wherein a gasket seal may be arranged around a periphery of the valve opening to seal between the axle end wall and a portion of the cap around the periphery of the valve opening, and wherein the intake opening may comprise a protrusion provided across at least a part of the intake opening. Thus, a protrusion is provided across the intake opening to ensure the gasket seal is retained in place as the intake opening moves with respect to the gasket seal.

The protrusion may be configured to at least partially compress the gasket seal while the gasket seal is adjacent to the intake opening. Thus, the gasket seal is held securely against the axle end wall.

An outer surface of the curved lateral wall may comprise a circumferential protrusion around a circumference of the axle, and the cap may comprise a retaining tooth configured to engage with the circumferential protrusion to prevent axial movement of the cap relative to the axle during rotation. Thus, the cap is retained on the axle which ensures a good seal is maintained and leakage is minimised, without requiring retaining teeth around the whole circumference of the cap.

The retaining tooth may be provided adjacent to the outlet tube. Thus, the tooth is placed in a convenient place to allow the tube to be used to snap-fit the cap to the axle.

The cap may comprise an inner wall arranged concentrically around the curved lateral wall of the axle, and an outer wall arranged concentrically around the inner wall such that a flow space is defined between the inner wall and the outer wall, the flow space being in liquid communication with the outlet tube.

The axle may be arranged on a valve base for attachment to an outer face of the ostomy appliance, and protrudes from the valve base away from the outer face of ostomy appliance in use.

Additionally, or alternatively, the axle end wall may generally planar.

Additionally, or alternatively, a gasket seal may be arranged around a periphery of the valve opening to seal between the axle end wall and a portion of the cap around the periphery of the valve opening.

Additionally, or alternatively, the cap may comprise an inner wall, the inner wall comprising:
- a generally cylindrical inner side wall portion; and
- an inner cap end portion;
  wherein the inner side wall portion defines a generally cylindrical cavity for receiving the axle such that the axle is rotatably arranged within the inner wall; and
- the inner cap end portion is arranged across the generally cylindrical cavity such that it overlies the axle end wall.

A gasket seal may be arranged on the axle end wall around a periphery of the valve opening to seal between the axle end wall and a planar face of the inner cap end portion.

An intake opening may be provided in the inner cap end portion, the intake opening being arranged to be rotatable into a position in which the intake opening at least partially aligns with the valve opening, such that the outlet element is in the open configuration. The outlet element may be rotatable from a fully open position in which the intake opening is fully aligned with the valve opening to a fully closed position in which the valve opening is obstructed by the inner cap end portion such that no liquid may pass from the hollow bore of the axle to the flow space through the valve opening. The inner cap end portion may be generally planar. The cap may further comprise an outer wall arranged concentrically around the inner wall such that a flow space is defined between the inner wall and the outer wall, the flow space being in liquid communication with the outlet tube. The outer wall may comprise an outer side wall portion and an outer cap end portion, wherein the outer cap end portion overlies the inner cap end portion and is axially spaced from the inner cap end portion such that at least a portion of the flow space is arranged between the outer cap end portion and the inner cap end portion.

Additionally, or alternatively, an axis of rotation of the outlet element defined by the axle may be perpendicular to the elongate axis of the outlet tube and optionally wherein the axis of rotation is perpendicular to the body of the ostomate in use. The axle end wall may be arranged transverse to the axis of rotation, and optionally perpendicular to the axis of rotation defined by the axle.

The present disclosure also provides an ostomy appliance comprising:
- an outlet valve as described above; and
- an ostomy bag wherein the outlet valve is attached to an outer face of the ostomy bag. In the closed configuration the outlet element substantially may overlie a cavity of the ostomy bag; and in the open configuration at least a portion of the outlet element may extend across a lower edge of the cavity of the ostomy bag.

Aspects of the present disclosure provide for an outlet valve for an ostomy appliance comprising: an axle defining a hollow bore for receiving a liquid output from the ostomy appliance, the axle comprising a curved lateral wall; and an outlet element comprising a cap arranged concentrically with the axle and an outlet tube affixed to the cap; wherein a valve opening is defined in the curved lateral wall; and the cap is rotatable around the axle to move from a closed configuration in which the valve opening is not in liquid communication with the outlet tube to an open configuration in which the valve opening is in liquid communication with the outlet tube; wherein the outlet valve further comprises at least one seal configured to provide sealing between the cap and the axle around a circumference of the axle and sealing between the intake opening and the valve opening when the outlet element is in the closed configuration.

The valve is thus less prone to leaks as sealing is provided both around a circumference of the axle, preventing leakage between the axle and cap, and also between the valve opening and intake opening when the outlet element is in the closed configuration, preventing leakage from the valve opening to the intake opening when the valve is closed.

In some embodiments, the at least one seal comprises a continuous first seal configured to provide sealing between the cap and the axle around a circumference of the axle and wherein the distance between the first seal and a basal end of the axle varies around the circumference of the axle. Thus, as the distance between the first seal and basal end of the axle varies around the circumference of the axle, the first seal may be arranged to provide sealing between the intake opening and the valve opening when the outlet element is in the closed configuration.

In some embodiments, the at least one seal comprises a first seal configured to provide sealing around a perimeter of the intake opening when the outlet element is in the closed position, the first seal being integrally formed with a second seal configured to provide sealing between the cap and the axle around a circumference of the axle.

In a further aspect, the present disclosure provides an outlet valve for an ostomy appliance comprising:
  an axle defining a hollow bore for receiving a liquid output from the ostomy appliance, the axle comprising a curved lateral wall; and
  an outlet element comprising a cap arranged concentrically with the axle and an outlet tube affixed to the cap, the outlet tube comprising an intake opening;
wherein:
  a valve opening is defined in the axle;
  the cap is rotatable around the axle to move the outlet element from a closed configuration in which the valve opening is not in liquid communication with the outlet tube to an open configuration in which the valve opening is in liquid communication with the outlet tube; and
  a first seal is configured to provide sealing between the cap and the axle around a perimeter of the intake opening when the outlet element is in the closed configuration, the first seal being integrally formed with a second seal configured to provide sealing between the cap and the axle around a circumference of the axle.

As described above, the seal may provide sealing between the intake opening and valve opening when the outlet element is in the closed configuration. Accordingly, in some embodiments there is provided an outlet valve for an ostomy appliance comprising: an axle defining a hollow bore for receiving a liquid output from the ostomy appliance, the axle comprising a curved lateral wall; and an outlet element comprising a cap arranged concentrically with the axle and an outlet tube affixed to the cap; wherein a valve opening is defined in the curved lateral wall; and the cap is rotatable around the axle to move from a closed configuration in which the valve opening is not in liquid communication with the outlet tube to an open configuration in which the valve opening is in liquid communication with the outlet tube; wherein the outlet valve further comprises at least one seal configured to provide sealing between the cap and the axle around a circumference of the axle and sealing between the intake opening and the valve opening when the outlet element is in the closed configuration, wherein the at least one seal comprises a first seal configured to provide sealing around a perimeter of the intake opening when the outlet element is in the closed position, the first seal being integrally formed with a second seal configured to provide sealing between the cap and the axle around a circumference of the axle.

Additionally, or alternatively, the axle may comprise an axle end wall, wherein the axle end wall is optionally generally planar.

Additionally, or alternatively, the valve opening may be arranged in a curved lateral wall of the axle. The first seal may comprise a gasket seal arranged on the curved lateral wall of the axle, the first seal being spaced apart from the valve opening around the circumference of the axle. The gasket seal may have a profile corresponding to the shape of the intake opening. The outlet tube may be configured to rotate with the cap such that on rotation of the cap the intake opening of the outlet tube is moved between an open position in which the intake opening is in liquid communication with the valve opening and a closed position in which the intake opening is not in liquid connection with the valve opening. In the closed position the first seal may be aligned with and arranged around a periphery of the intake opening, thereby providing a seal between the intake opening and the curved lateral wall of the axle.

Additionally, or alternatively, the cap may comprise a curved cap wall defining a generally cylindrical cavity for receiving the axle such that the axle is rotatably arranged within the curved cap wall. The second seal may be arranged around the circumference of the axle between the curved cap wall and the axle, at an axial position between the intake opening and a distal end of the curved cap wall.

Additionally, or alternatively, the axle may be arranged on a valve base for attachment to an outer face of the ostomy appliance, and may protrude from the valve base away from the outer face of ostomy appliance in use.

Additionally, or alternatively, a third, circumferential seal may be arranged between the valve base and the cap at an axial position between a proximal end of the cap and the valve opening.

Additionally, or alternatively, an axis of rotation of the outlet element defined by the axle may be perpendicular to the elongate axis of the outlet tube and optionally the axis of rotation may be perpendicular to the body of the ostomate in use.

According to the further aspect, the present disclosure also provides an ostomy appliance comprising:
  an outlet valve as described above; and
  an ostomy bag;
wherein the outlet valve is attached to an outer face of the ostomy bag. In the closed configuration the outlet element may substantially overlie a cavity of the ostomy bag; and in the open configuration at least a portion of the outlet element may extend across a lower edge of the cavity of the ostomy bag.

Thus, in a further aspect, the present disclosure provides an outlet valve for an ostomy appliance comprising:
- an axle defining a hollow bore for receiving a liquid output from the ostomy appliance, the axle comprising a curved lateral wall; and
- an outlet element comprising a cap arranged concentrically with the axle and an outlet tube affixed to the cap;
- wherein a valve opening is defined in the curved lateral wall; and
- the cap is rotatable around the axle to move from a closed configuration in which the valve opening is not in liquid communication with the outlet tube to an open configuration in which the valve opening is in liquid communication with the outlet tube;
- wherein the outlet valve further comprises a continuous first seal configured to provide sealing between the cap and the axle around a circumference of the axle; and
- wherein a distance between the first seal and a basal end of the axle varies around the circumference of the axle.

As described above, the seal may provide sealing between the cap and the axle around a circumference of the axle and sealing between the intake opening and the valve opening when the outlet element is in the closed configuration. Accordingly, in some embodiments there is provided an outlet valve for an ostomy appliance comprising: an axle defining a hollow bore for receiving a liquid output from the ostomy appliance, the axle comprising a curved lateral wall; and an outlet element comprising a cap arranged concentrically with the axle and an outlet tube affixed to the cap; wherein a valve opening is defined in the curved lateral wall; and the cap is rotatable around the axle to move from a closed configuration in which the valve opening is not in liquid communication with the outlet tube to an open configuration in which the valve opening is in liquid communication with the outlet tube; wherein the outlet valve further comprises at least one seal configured to provide sealing between the cap and the axle around a circumference of the axle and sealing between the intake opening and the valve opening when the outlet element is in the closed configuration, wherein the at least one seal comprises a continuous first seal configured to provide sealing between the cap and the axle around a circumference of the axle and wherein the distance between the first seal and a basal end of the axle varies around the circumference of the axle.

Additionally, or alternatively, the first seal may follow a curved or stepped path around the curved lateral wall.

Additionally, or alternatively, at a first circumferential position of the axle, the first seal may be at a distance from the basal end that is less than or equal to a distance from the basal end to a proximal edge of the valve opening. At second circumferential position of the axle, the first seal may be at a distance from the basal end that is greater than or equal to a distance from the basal end to a distal edge of the valve opening. The first circumferential position may be opposite the second circumferential of the annular seal. The outlet element may be rotatable to a fully open position wherein; the outlet element is in the open configuration; and wherein the intake opening is fully aligned with the valve opening. In the closed configuration the intake opening may be arranged at the second circumferential position, such that the first seal is arranged between the intake opening and the valve opening. The first circumferential position may be a circumferential position of the of the valve opening.

Additionally, or alternatively, an annular second seal may be arranged around a circumference of the axle. A distance between the annular second seal and a basal end of the axle may be constant around the circumference of the axle. The annular second seal may be arranged between the basal end of the axle and a proximal edge of the valve opening.

Additionally, or alternatively, the outlet tube may comprise an intake opening, wherein the outlet tube is configured to rotate with the cap such that on rotation of the cap the intake opening of the outlet tube is moved between an open configuration in which the intake opening is in liquid communication with the valve opening and a closed configuration in which the intake opening is not in liquid connection with the valve opening. In the open configuration at least a part of the intake opening may be arranged between the valve opening and the first seal such that at least a portion of the intake opening is in liquid communication with the valve opening.

Additionally, or alternatively, the cap may comprise a curved cap wall defining a generally cylindrical cavity for receiving the axle such that the axle is rotatably arranged within the curved cap wall. The cap may further comprise a cap end portion extending across a front end of the generally cylindrical cavity.

Additionally, or alternatively, the axle may be arranged on a backing flange for attachment to an outer face of the ostomy appliance, and may protrude from the backing flange away from the outer face of ostomy appliance in use.

Additionally, or alternatively, an axis of rotation of the outlet element defined by the axle may be arranged perpendicular to the elongate axis of the outlet tube and optionally the axis of rotation may be perpendicular to the body of the ostomate in use.

According to the further aspect, the present disclosure also provides an ostomy appliance comprising:
- an outlet valve as described above; and
- an ostomy bag wherein the outlet valve is attached to an outer face of the ostomy bag. In the closed configuration the outlet element may substantially overlie a cavity of the ostomy bag; and in the open configuration at least a portion of the outlet element may extend across a lower edge of the cavity of the ostomy bag.

BRIEF DESCRIPTION OF THE DRAWINGS

One or more aspects of the disclosure will now be described, by way of example only, with reference to the accompanying drawings in which.

DETAILED DESCRIPTION

Figure 1:
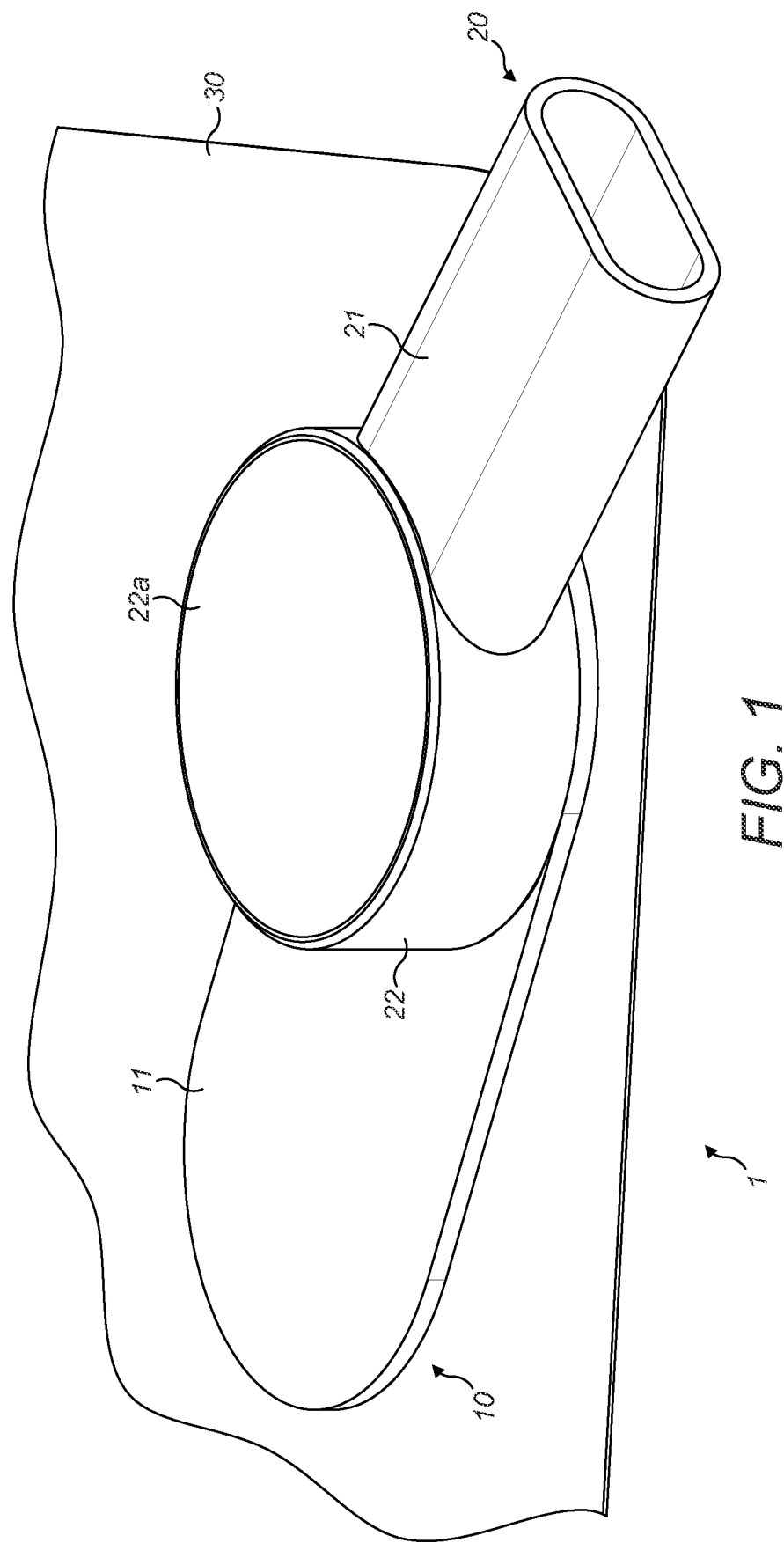
FIG. 1 illustrates a schematic perspective view of an outlet valve according to a first aspect of the present disclosure.

In the following description, the equivalent reference numerals are used in different aspects to denote equivalent or similar features.

Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to exemplar aspects of the disclosure. The description of the aspects is not meant to include all the possible aspects of the disclosure that are claimed in the appended claims. Many modifications, improvements and equivalents which are not explicitly recited in the following aspects may fall within the scope of the appended claims. Features described as part of one aspect may be combined with features of one or more other aspects unless the context clearly requires otherwise.

In this specification, the use of the singular includes the plural unless the context clearly dictates otherwise. In this specification, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

A first example outlet valve 1 for an ostomy appliance according to the present disclosure is shown in FIGS. 1 to 4. The ostomy appliance may comprise an ostomy bag 30 (shown in FIG. 1) and the outlet valve 1, the outlet valve 1 being attached to an outer face of the ostomy bag 30, preferably to an outer face of an outer wall of the ostomy bag 30.

The outlet valve 1 comprises an outlet element 20 and an axle 13 defining a hollow bore 14 for receiving a liquid output from the ostomy bag 30. The outlet element 20 comprises a cap 22 arranged concentrically with the axle 13, and an outlet tube 21 affixed to the cap 22. The cap 22 is rotatable around the axle 13, about an axis of rotation 25 defined by the axle 13, to move the outlet element 20 from a closed configuration in which a valve opening 15 arranged through the axle 13 is not in liquid communication with the outlet tube 21 to an open configuration in which the valve opening 15 is in fluid communication with the outlet tube 21.

The outlet valve 1 may be configured such that when the outlet element 20 is in the open configuration, a flow path for liquid from the ostomy bag 30 may be defined through the hollow bore 14, through the valve opening 15 and the cap 22 and into the outlet tube 21 for discharge from an outlet opening 24 of the outlet tube 21. In the closed configuration, flow of liquid along the flow path is interrupted such that liquid may not flow into the outlet tube 21.

A valve base 10 of the outlet valve 1 may be configured for attachment to the outer face of the ostomy bag 30 and may comprise a backing flange 11 having a generally planar attachment face 12 arranged on a back side of the valve base 10 (i.e. a face configured to be proximal to the body of the ostomate in use). The generally planar attachment face 12 may be attachable to the outer face of the ostomy bag 30, for example by welding or by using an adhesive. The valve base 10 may comprise the axle 13. The axle may protrude from an outer face 18 of the backing flange 11. The axle 13 may be integrally formed with the backing flange 11, for example by moulding.

The valve opening 15 is provided through the axle 13 for receiving a liquid output from the ostomy bag 30. The outlet valve 1 may be arranged overlying an ostomy bag aperture provided in a wall of the ostomy bag 30. Liquid from the ostomy bag aperture may thereby pass through the hollow bore 14 to the valve opening 15. When the outlet element 20 is in the closed configuration, the valve opening 15 is not in liquid communication with the outlet tube 21. When the outlet element 20 is in the open configuration the valve opening 15 is in liquid communication with the outlet tube 21.

The axle 13 may comprise a curved lateral wall 13*a* and an axle end wall 13*b*, the axle end wall 13*b* being arranged across the hollow bore 14. The axle end wall 13*b* may be generally planar. The axle end wall 13*b* may be arranged transverse and optionally perpendicular to the axis of rotation 25 defined by the axle 13.

Figure 2:
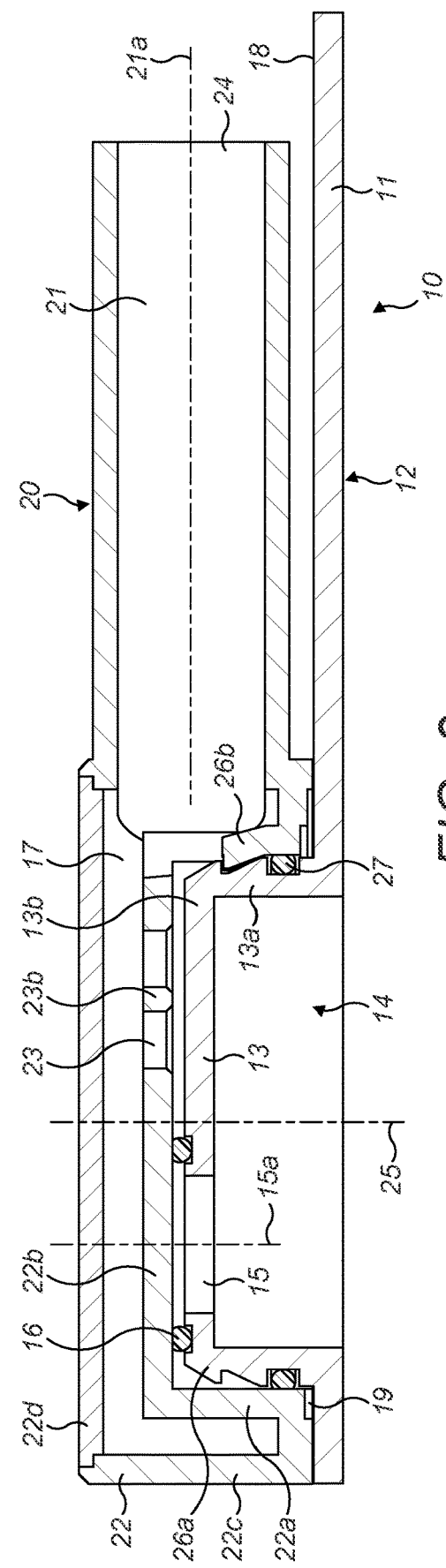
FIG. 2 illustrates a schematic cross-sectional view of the outlet valve of FIG. 1 in a closed configuration.
Figure 3:
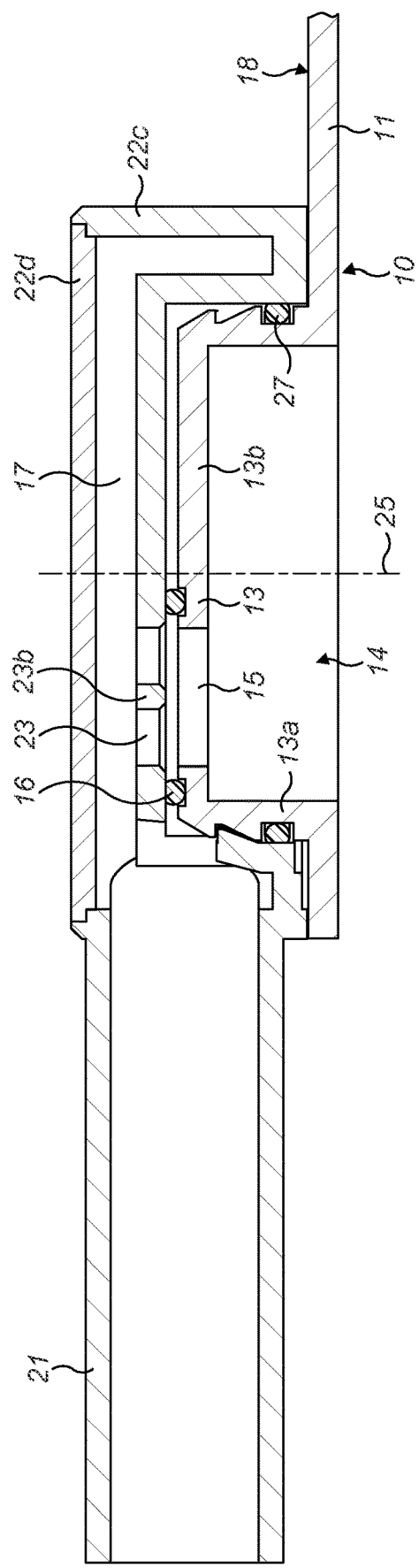
FIG. 3 illustrates a schematic partial cross-sectional view of the outlet valve of FIG. 1 in an open configuration.
Figure 4:
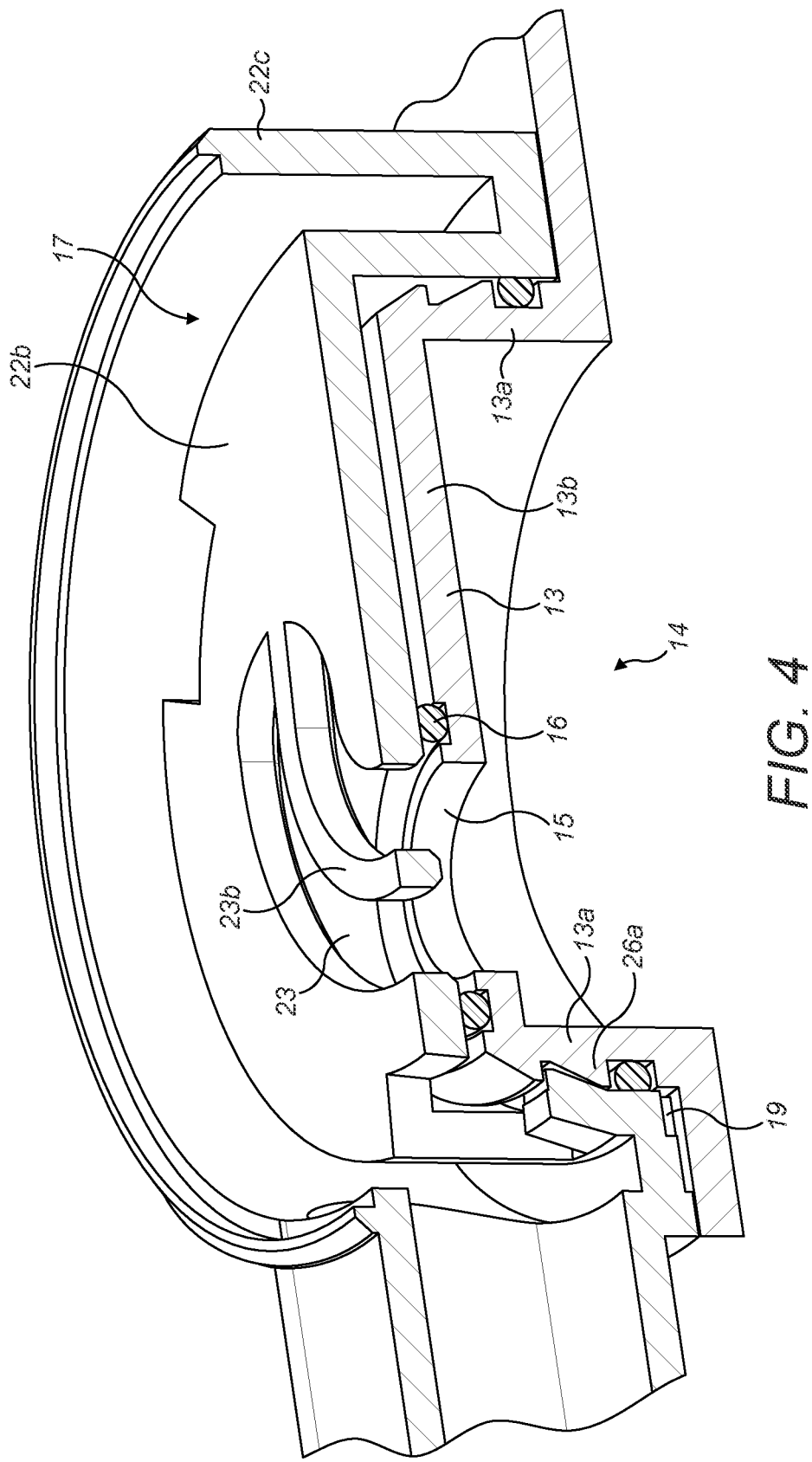
FIG. 4 illustrates a schematic partial perspective view of the outlet valve of FIG. 1 in an open configuration.
Figure 5A:
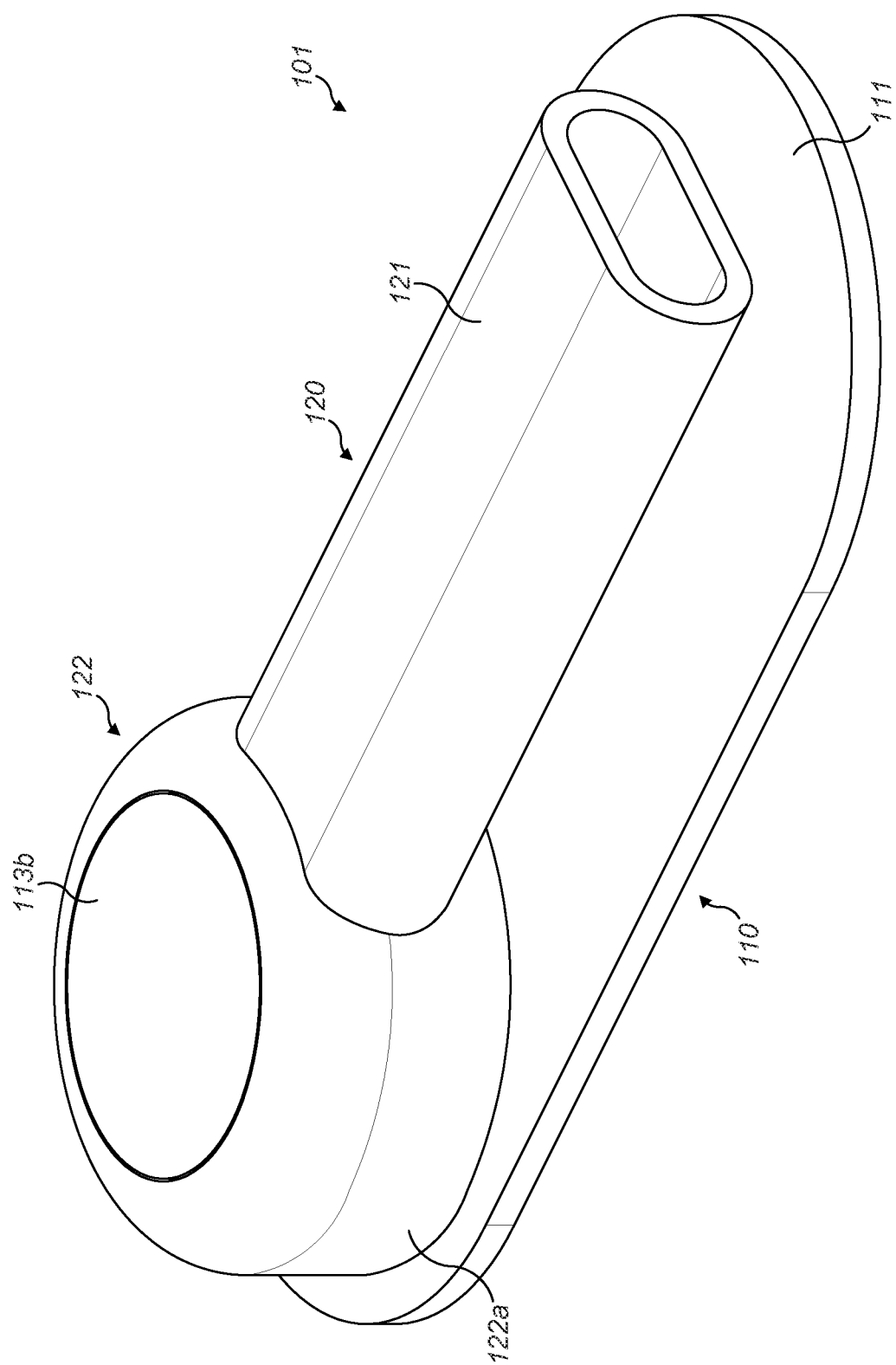
FIG. 5a illustrates a schematic perspective view of an outlet valve according to a second aspect of the present disclosure.
Figure 5B:
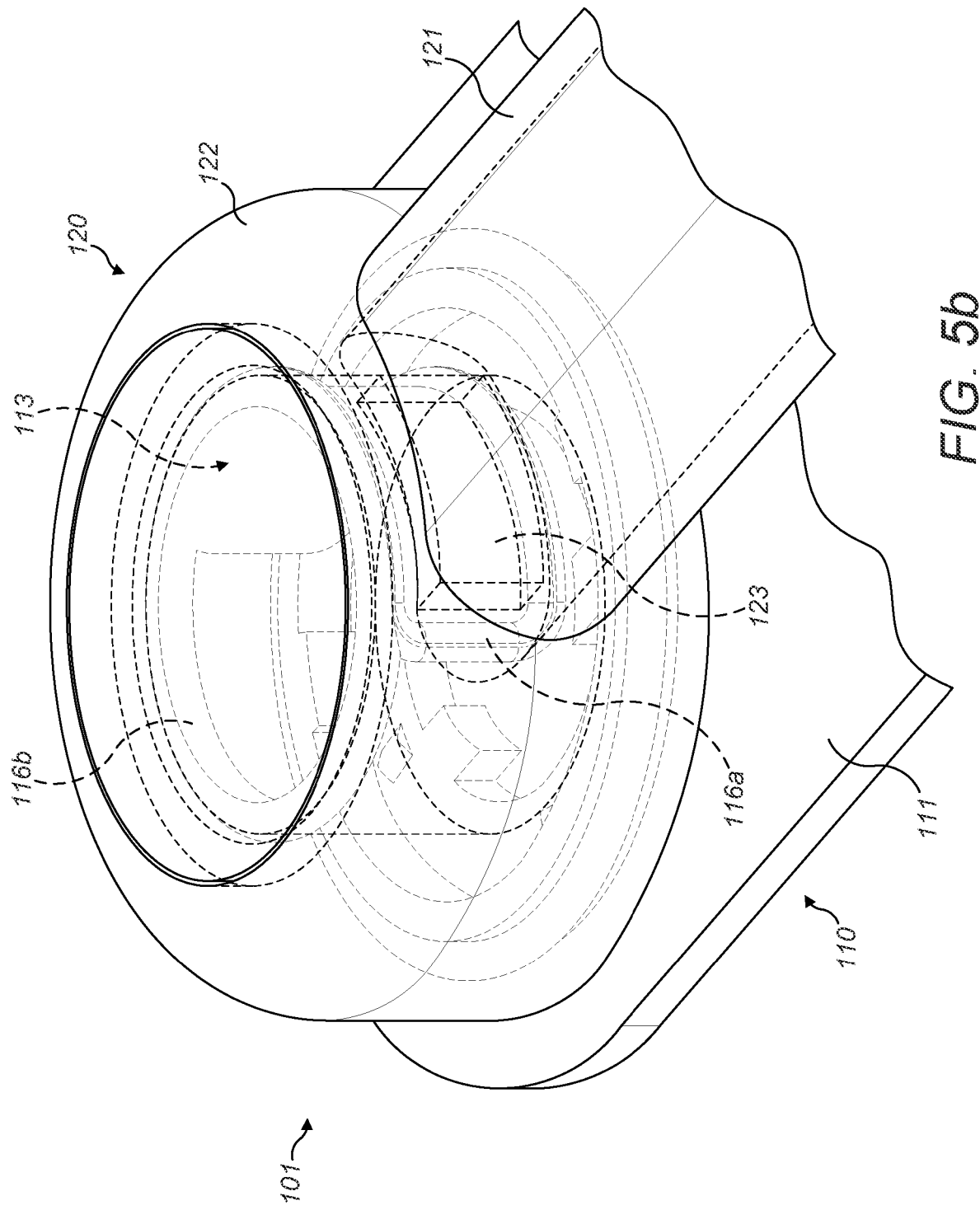
FIG. 5b illustrates a schematic partial perspective view of the outlet valve of FIG. 5a showing hidden detail.

The valve opening 15 may be defined in a portion of the axle end wall 13*b*, as shown in FIGS. 2 to 4. The valve opening 15 may have a generally circular shape. A gasket seal 16 may be arranged around a periphery of the valve opening 15 to seal between the axle end wall 13*b* and a portion of the cap 22 around the periphery of the valve opening 15 such that liquid cannot pass into any space defined between the axle end wall 13*b* and the cap 22.

The cap 22 may comprise an inner wall, the inner wall comprising an inner side wall portion 22*a* which may be generally cylindrical and an inner cap end portion 22*b*. The inner side wall portion 22*a* may define a generally cylindrical cavity for receiving the axle 13 such that the axle 13 is rotatably arranged within the inner wall.

The inner cap end portion 22*b* may be generally planar. It may be arranged across the generally cylindrical cavity such that it overlies the axle end wall 13*b*. The gasket seal 16 may be arranged on the axle end wall 13*b* around a periphery of the valve opening 15 to seal between the axle end wall 13*b* and a generally planar back face of the inner cap end portion 22*b*.

The intake opening 23 may be provided in the inner cap end portion 22*b* and may be in liquid communication with the outlet tube 21. The intake opening 23 being arranged to be rotatable into a position in which the intake opening 23 at least partially aligns with the valve opening 15 to define a liquid path therethrough, such that the outlet element 20 is in the open configuration. The intake opening 23 may have a width which is substantially equal to a diameter of the valve opening 15. The intake opening 23 may have an arcuate shape aligned with a circumference around the axis of rotation 25, a central axis 15*a* of the valve opening 15 being arranged on the same circumference. The arcuate shape may allow the full alignment of the valve opening 15 with the intake opening 23 at a range of angular positions of the cap 22. A protrusion 23b may be provided across at least a part of the intake opening 23 to partially compress the gasket seal while the gasket seal 16 is adjacent to the intake opening 23. This may limit bulging of the gasket seal 16 into the opening 23b and so may limit pinching or slicing of the gasket seal 16 on contact with the edges of the intake opening 23 on movement of the cap 22.

The cap 22 may comprise an outer wall arranged concentrically around the inner wall such that a flow space 17 is defined between the inner wall and the outer wall, the flow space 17 being in liquid communication with the outlet tube 21. The intake opening 23 may provide a liquid flow path into the flow space 17 from the valve opening 15. The outer wall may comprise an outer side wall portion 22c and an outer cap end portion 22d, wherein the outer cap end portion 22d overlies the inner cap end portion 22b and is axially spaced from the inner cap end portion 22b such that at least a portion of the flow space 17 is arranged between the outer cap end portion 22d and the inner cap end portion 22b. The outer cap end portion 22d may be formed as a separate part to facilitate manufacture and assembly of the cap 22 and may be affixed to the outer side wall portion 22c by adhesive or mechanical clips. A seal (not shown) may be provided between the outer cap end portion 22d and the outer side wall portion 22c.

The inner side wall portion 22a and the outer side wall portion 22c may be joined at their basal ends (i.e. the end proximal to the backing flange 11 of the valve base 10) by an annular flange such that there is no liquid flow path out of the flow space 17 at the basal end of the cap 22.

The axle 13 may be retained in the cap 22 by one or more retention features. The retention features may be in the form of one or more interengaging protrusions 26a, 26b arranged on an outer face of the curved lateral wall 13a of the axle 13 and an inner face of the inner side wall portion 22a. The interengaging protrusions 26a, 26b may be configured to prevent axial movement of the cap 22 relative to the axle 13 during rotation.

A further seal 27 maybe arranged between an outer face of the curved lateral wall 13a of the axle 13 and an inner face of the inner side wall portion 22a at a basal end of the axle 13 to prevent fluid egress between the cap 22 and the axle 13 at the basal end of the axle 13.

One or more detents 19 may be provided on the backing flange 11 of the valve base 10 for co-operating with one or more recesses or protrusions arranged on the cap 22. The detent(s) 19 may be positioned to provide audible and/or tactile feedback to confirm the rotation position of the outlet element 20 to the user, and thereby to confirm when the outlet element 20 is in the open and/or closed configurations.

The outlet tube 21 may extend laterally from the cap 22 such that the axis of rotation 25 of the outlet element 20 defined by the axle 13 is perpendicular to an elongate axis 21a of the outlet tube 21.

In use, the outlet element 20 may be rotatable such that the outlet tube 21 moves through an arc of rotation from an upward-pointing position at a first end of the arc of rotation to a downward-pointing position at a second end of the arc of rotation (as shown in FIG. 1).

At the first end of the arc of rotation, the outlet element 20 may be in the closed configuration. The user may rotate the outlet element 20 downwards by rotating the cap 22 to a limit position. The limit position may be defined at a point on the arc of rotation furthest from its first end at which the outlet element 20 is still in the closed configuration. As the outlet element 29 is rotated from the limit position towards the second end of the arc of rotation the valve opening 15 and the intake opening 23 will become gradually move into alignment, increasing the area of the flow path gradually until reaching a fully open configuration in which the valve opening 15 and the intake opening 23 are aligned. The position at which the outlet element is in a fully open configuration, i.e. in which the base and intake openings are fully aligned, may coincide with the second end of the arc of rotation.

Therefore, at the first end of the arc of rotation the outlet element 20 may be in a fully closed position in which the valve opening 15 is obstructed by the inner cap end portion 22b such that no liquid may pass from the hollow bore 14 of the axle 13 to the flow space 17 through the valve opening 15. At the second end of the arc of rotation, the outlet element 20 may be in a fully open position in which the intake opening 23 is fully aligned with the valve opening 15.

The circumferential position of the valve opening 15 and the intake opening 23 may be arranged such that when the intake opening 23 is fully aligned with the valve opening 15 and the outlet element 20 is in the open configuration, the outlet tube 21 is directed generally downwards. At the first end of the arc of rotation, with the outlet element in the closed configuration, an outlet opening 24 of the outlet tube 21 may be arranged generally upward and/or may overlie the backing flange 11.

The outlet valve 1 may be configured such that, in use, the axis of rotation 25 is arranged generally horizontally but perpendicular to an attachment face 12 of the backing flange 11 of the valve base 10.

Further examples of an outlet valve according to the present disclosure are described below. Only those features that differ in this aspect compared to the previous aspect will be described in detail in the following description. For features that are common to one or more aspects, reference should be made to the description as a whole.

A second example outlet valve 101 according to the present disclosure is shown in FIGS. 5a to 7. The outlet valve 101 comprises an axle 113 and a cap 122.

Figure 6:
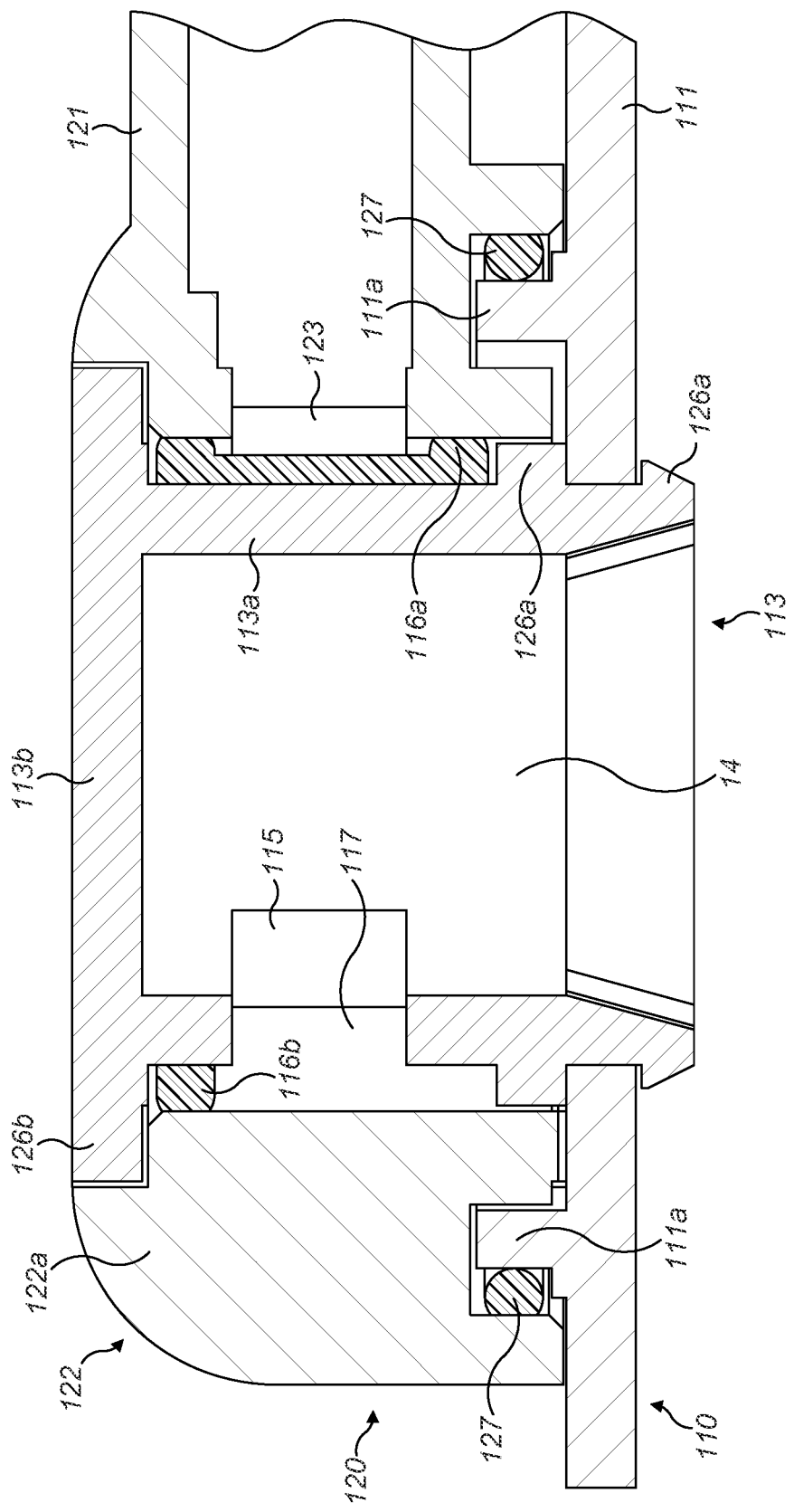
FIG. 6 illustrates a schematic partial cross-sectional view of the outlet valve of FIG. 5a in a closed configuration.
Figure 7:
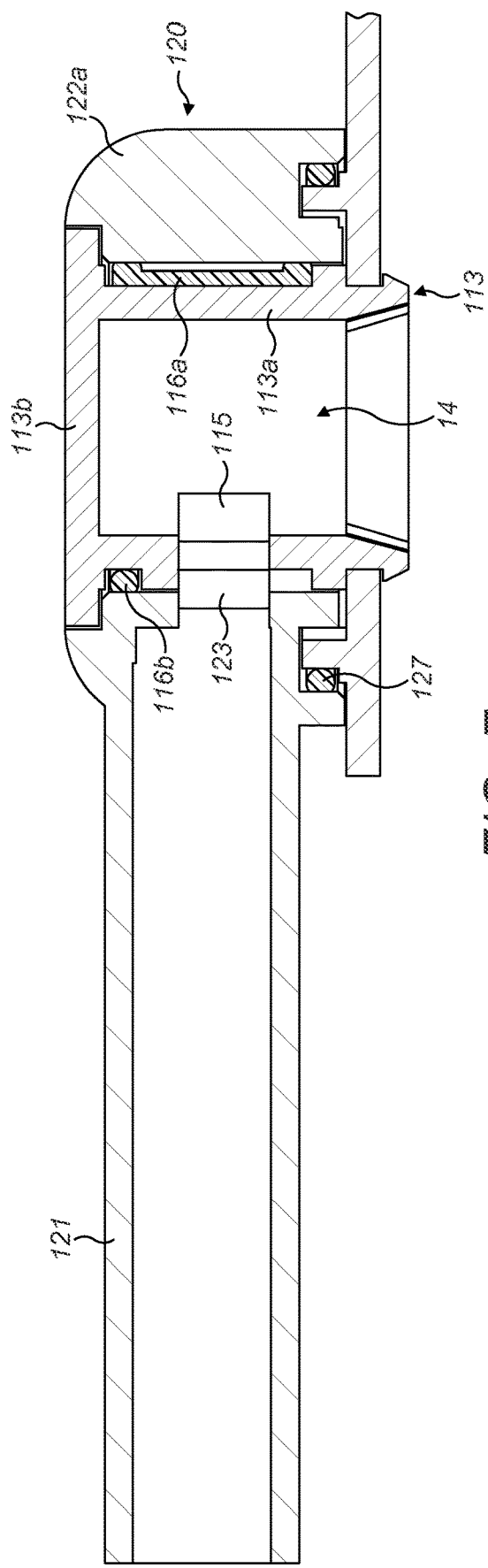
FIG. 7 illustrates a schematic partial cross-sectional view of the outlet valve of FIG. 5a in an open configuration.

A valve base 110 of the outlet valve 101 may comprise a backing flange 111 and the axle 113, the axle 113 defining the hollow bore 14. The axle 113 may be moulded as a separate component to the backing flange 111, the axle 113 being affixed to the backing flange 111, for example using a snap or interference fit of retention features 126a and 126b as shown in FIGS. 6 and 7. No liquid path may be defined through the axle end wall 113b.

A valve opening 115 is provided through the axle 113 for receiving a liquid output from the ostomy bag. The axle 113 may comprise a curved lateral wall 113a and an axle end wall 113b, the axle end wall 113b being arranged across the hollow bore 14.

The axle 113 may extend through the full height of the valve such that the axle end wall 113b comprises a front face of the outlet valve 101 (i.e. it is not covered by the cap 122 of the outlet element 120).

The valve opening 115 may be defined in a portion of the curved lateral wall 113a of the axle 113 as shown in FIGS. 6 and 7.

An outlet element 120 of the outlet valve 101 may comprise the cap 122 and an outlet tube 121. The cap 122 may comprise a curved cap wall 122a defining a generally cylindrical cavity for receiving the axle 113 such that the axle is rotatably arranged within the curved cap wall 122a. The cap 122 may therefore have a generally annular shape.

The outlet tube 121 may be integrally formed with or affixed to the cap 122. The outlet tube 121 comprises an intake opening 123 at its inner end, arranged through the curved cap wall 122a. The intake opening 123 may be configured to receive liquid from the valve opening 115 when the outlet valve 101 is in the open configuration.

The cap 122 may be arranged concentrically with the axle 113 such that the cap 122 is rotatable about the axle 113. The outlet tube 121 may be affixed to the cap 122 such that it rotates with the cap 122 about the axle 113. Therefore, on rotation of the outlet element 120 including the cap 122 the intake opening 123 of the outlet tube 121 may be moved between an open position in which the intake opening 123 is in liquid communication with the valve opening 115 (such that the outlet element is in the open configuration) and a closed position in which the intake opening 123 is not in liquid connection with the valve opening 115 (such that the outlet element is in the closed configuration).

A circumferential position of the valve opening 115 around the axle 113 may be arranged such that when the intake opening 123 is aligned with the valve opening 115, i.e. the outlet element 120 is in the open configuration, the outlet tube 121 is directed generally downwards. The intake opening 123 may have a shape and size which is substantially the same as the size and shape of the valve opening 115. The intake opening 123 and the valve opening 115 may be arranged at the same axial distance from the valve base 110.

A first seal 116a may be provided to seal between the cap 122 and the axle 113 around a perimeter of the intake opening 123 when the outlet element 120 is in the closed configuration. The first seal 116a may be integrally formed with a second seal 116b configured to provide sealing between the cap 122 and the axle 113 around a circumference of the axle 113.

The first seal 116a may comprise a gasket seal arranged on the curved cap wall 122a of the axle, the first seal 116a being spaced apart from the intake opening 123 around the circumference of the axle 113

The gasket seal forming the first seal 116a may have a profile corresponding to the shape of the intake opening 123. When the outlet element 120 is in the closed position, the first seal 116a may be aligned with and arranged around a periphery of the intake opening 123, thereby providing a seal between the intake opening 123 and the curved lateral wall of the axle 113 such that the outlet tube 121 is not in liquid communication with the valve opening 115.

The second seal 116b may be arranged around the circumference of the axle 113 between the curved cap wall 122a and the axle 113, at an axial position between the valve opening 115 and a front end of the curved cap wall 122a (i.e. an end of the curved cap wall distal to the backing flange 111 of the valve base 110.

The first seal 116a and second seal 116b may be configured to be stationary relative to the axle 113. The first seal 116a and second seal 116b may be attached to the axle 113 such that they do not rotate relative to the axle 113 on rotation of the cap 122, for example due to resilience of the first and second seals 116a, 116b, using adhesive or by provision of a groove on the axle 113 on in which the first seal 116a and second seal 116b may be received.

In use, the outlet element 120 may be rotatable such that the outlet tube 121 moves through an arc of rotation from an upward-pointing position at a first end of the arc of rotation to a downward-pointing position at a second end of the arc of rotation. At the first end of the arc of rotation, the outlet element 120 may be in the closed configuration. The user may rotate the outlet element 120 downwards by rotating the cap 122 to a limit position. The limit position may be defined at a point on the arc of rotation furthest from its first end at which the outlet element 120 is still in the closed configuration. As the outlet element 120 is rotated from the limit position towards the second end of the arc of rotation the intake opening 23 will become gradually move out of alignment with the first seal 116a such that a flow path is defined from the valve opening 115 through the flow space 117 to the intake opening 123. As the outlet element 120 is rotated further from the first end of the arc of rotation, the area of the flow path may gradually increase until the outlet element 120 reaches a reaching a fully open position in which the valve opening 15 and the intake opening 123 are aligned. The fully open position may coincide with the second end of the arc of rotation.

A third, circumferential seal 127 may be arranged between the valve base 110 and the cap 122 (as shown in FIGS. 6 and 7). The third, circumferential seal 127 may be arranged between backing flange 111 and the cap 122, for example being received in a recess provided in a basal face of the curved cap wall 122a and abutting a sealing protrusion 111a provided on a front face of the backing flange 111. The third, circumferential seal 127 may therefore provide a seal between the valve base 110 and the cap 122 adjacent to a basal end of the axle 113 such that fluid entering a flow space 117 between the cap 122 and the axle 113 cannot pass out of the outlet valve 101 between the cap 122 and the valve base 110. In an alternative example, the third, circumferential seal 127 may be arranged between the axle 113 and the cap 122.

The relative axial positions of the backing flange 111, the axle 113 and the outlet element 120 may be fixed using retention features, for example in the form of a pair of basal flanges 126a provided at a basal end of the axle 113 and a distal flange 126b provided at a distal end of the axle 113. An aperture may be provided in the backing flange 111 to receive the axle 113. The pair of basal flanges 126a may be configured to receive a portion of the backing flange 111 therebetween to provide a push-fit assembly of the axle 113 to the backing flange 111. The distal flange 126b may extend outwards from the axle 113 to retain the outlet element 120 between the distal flange 126b and the backing flange 111.

Figure 8:
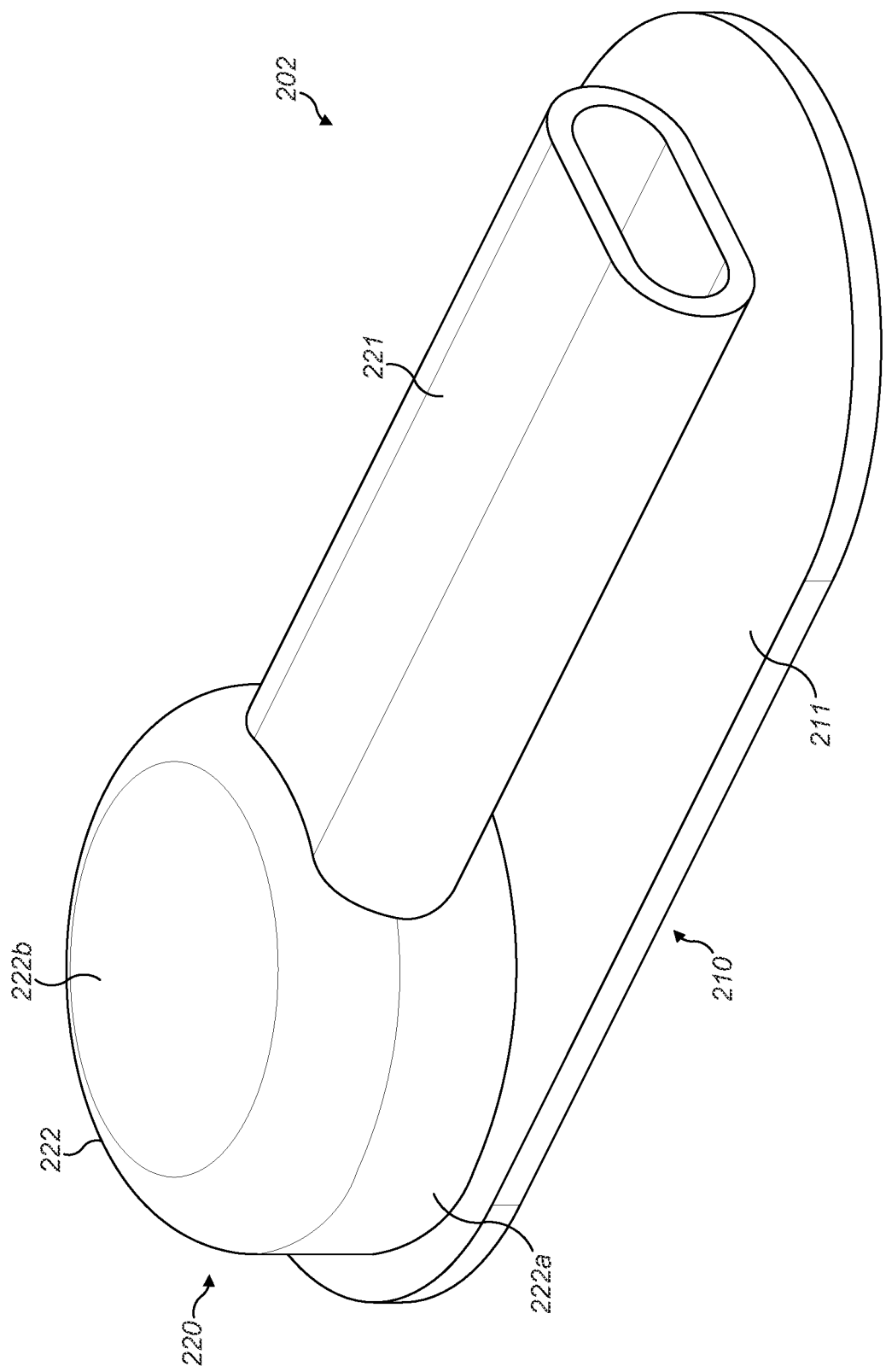
FIG. 8 illustrates a schematic perspective view of an outlet valve according to a third aspect of the present disclosure.
Figure 9:
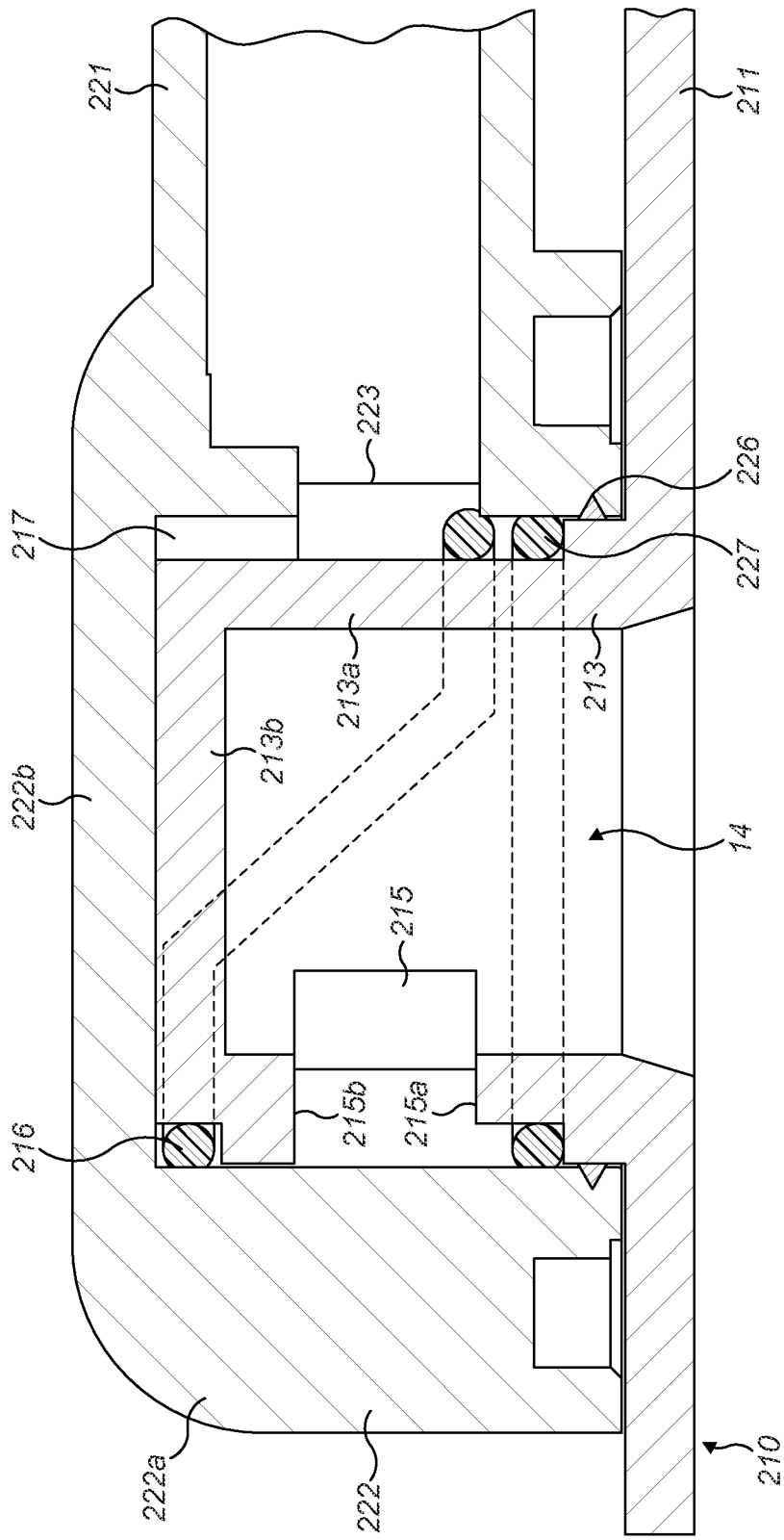
FIG. 9 illustrates a schematic partial cross-sectional view of the outlet valve of FIG. 8 in a closed configuration.
Figure 10:
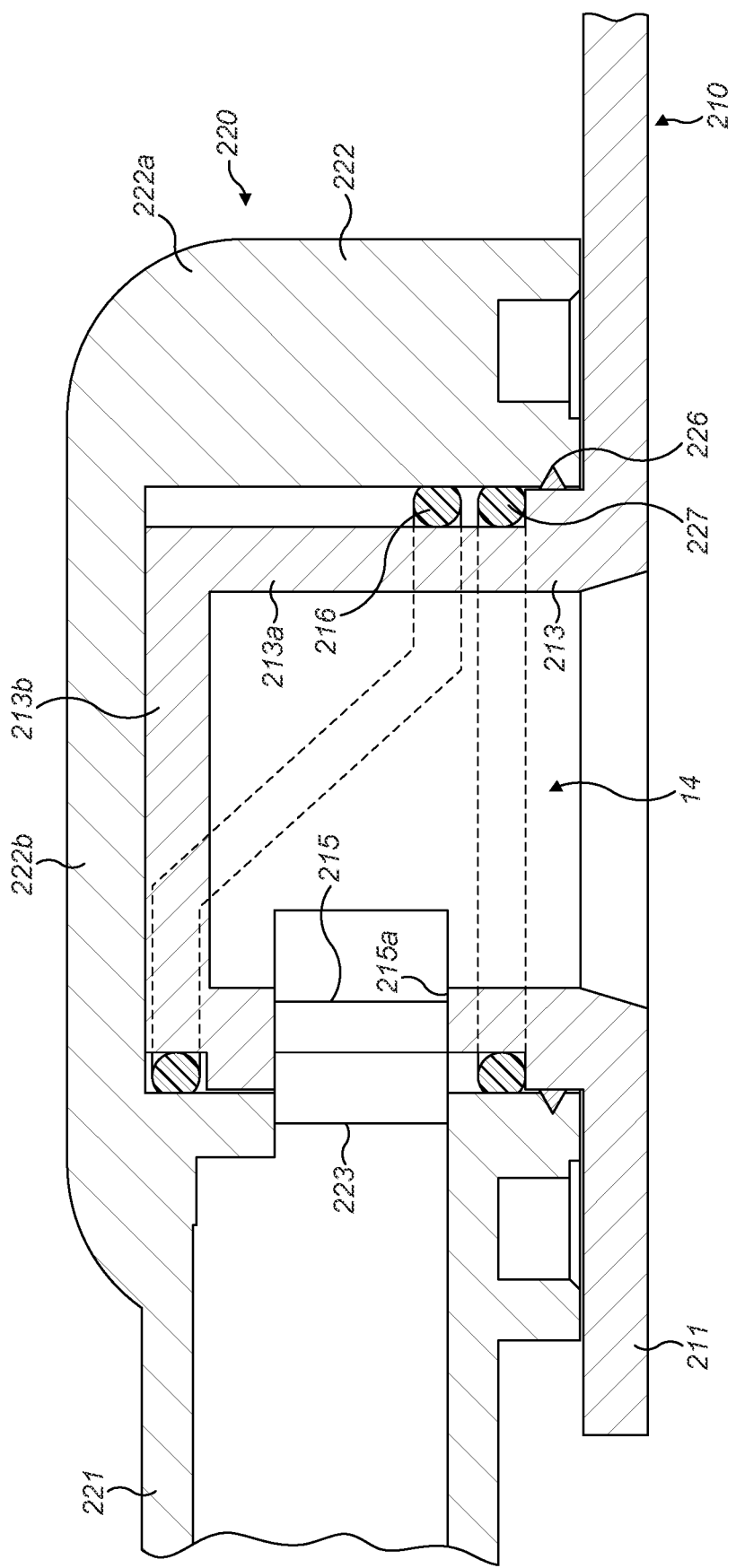
FIG. 10 illustrates a schematic partial cross-sectional view of the outlet valve of FIG. 8 in an open configuration.

A third example outlet valve 202 according to the present disclosure is shown in FIGS. 8 to 10. The outlet valve 202 comprises an axle 213 and a cap 222.

A valve base 210 of the outlet valve 202 may comprise a backing flange 211 and the axle 213, the axle 213 defining the hollow bore 14. The axle 213 may be integrally formed with the backing flange 211, for example by forming these as a single moulding.

A valve opening 215 is provided through the axle 213 for receiving a liquid output from the ostomy bag. The axle 213 may comprise a curved lateral wall 213a and an axle end wall 213b, the axle end wall 213b being arranged across the hollow bore 14. No liquid path may be defined through the axle end wall 213b. The valve opening 215 may be defined in a portion of the curved lateral wall 213a of the axle 213 as shown in FIGS. 9 and 10.

An outlet element 220 of the outlet valve 202 may comprise the cap 222 and an outlet tube 221. The cap 222 may comprise a curved cap wall 222a defining a generally cylindrical cavity for receiving the axle 213 such that the axle is rotatably arranged within the curved cap wall. The cap 222 may further comprise a cap end wall 222b arranged across and sealing the distal end of the generally cylindrical cavity.

The outlet tube 221 may be integrally formed with or affixed to the cap 222. The outlet tube 221 comprises an intake opening 223 at its inner end, arranged through the curved cap wall 222a. The intake opening 223 may be configured to receive liquid from the valve opening 215 when the outlet valve 202 is in the open configuration.

The cap 222 may be arranged concentrically with the axle 213 such that the cap 222 is rotatable about the axle 213. The outlet tube 221 may be affixed to the cap 222 such that it rotates with the cap 222 about the axle 213. Therefore, on rotation of the cap 222 the intake opening 223 of the outlet tube 221 may be moved between an open position in which the intake opening 223 is in liquid communication with the valve opening 215 and a closed position in which the intake opening 223 is not in liquid connection with the valve opening 215.

The intake opening 223 may have a shape and size which is substantially the same as the size and shape of the valve opening 215. The intake opening 223 and the valve opening 215 may be arranged at the same axial distance from the valve base 210.

On rotation of the cap 222, the outlet element 220 is moved between an open configuration in which the intake opening 223 is in liquid communication with the valve opening 215 and a closed configuration in which the intake opening 223 is not in liquid connection with the valve opening 215. A circumferential position of the valve opening 215 around the axle 213 may be arranged such that when the intake opening 223 is aligned with the valve opening 215, i.e. the outlet element 220 is in the open configuration, the outlet tube 221 is directed generally downwards.

The outlet valve may further comprise a first seal 216, which may be continuous, configured to provide sealing between the cap 222 and the axle 213 around a circumference of the axle 213. The first seal 216 may follow a curved or stepped path around the curved lateral wall 213*a* of the axle 213 such that a distance between the first seal 216 and a basal end of the axle 213 varies around the circumference of the axle 213, as measured parallel to an axis of rotation defined by the axle 213. The number or complexity of seals required to seal the outlet valve 202 may therefore be reduced.

At a first circumferential position of the axle 213, the first seal 216 may be positioned at a distance from the basal end of the axle 213 that is less than or equal to a distance from the basal end of the axle 213 to a proximal edge 215*a* of the valve opening 215. The first circumferential position may be a circumferential position of the of the valve opening 215. The first circumferential position may extend around an arc of the circumference corresponding to the arc of the circumference along which the valve opening 215 extends.

At a second circumferential position of the axle 213, the first seal 216 is at a distance from the basal end of the axle 213 that is greater than or equal to a distance from the basal end of the axle 213 to a distal edge 215*b* of the valve opening. The second circumferential position may extend around an arc of the circumference corresponding to the arc of the circumference along which the valve opening 215 is arranged when the outlet element 220 is in the closed configuration.

The first circumferential position may be arranged opposite the second circumferential of the first seal 216, i.e. the first circumferential position may be arranged approximately 180 degrees around the circumference of the axle 213 from the second circumferential position.

An annular second seal 227 may be arranged around a circumference of the axle 213 for sealing a flow space 217 arranged between the cap 222 and the axle 213 adjacent to the basal end of the axle 213. The annular second seal 227 may be arranged between the basal end of the axle 213 and the first seal 216 such that the annular second seal 227 may be arranged between the basal end of the axle 213 and a proximal edge 215*a* of the valve opening 215. A distance between the annular second seal 227 and a basal end of the axle 213 may be constant around the circumference of the axle 213.

In use, the outlet element 220 may be rotatable such that the outlet tube 221 moves through an arc of rotation from an upward-pointing position at a first end of the arc of rotation to a downward-pointing position at a second end of the arc of rotation. At the first end of the arc of rotation, the outlet element 220 may be in the closed configuration. In the closed configuration, the intake opening 223 may be arranged at the second circumferential position, such that the first seal 216 is arranged between the intake opening 223 and the valve opening 215.

The user may rotate the outlet element 20 downwards by rotating the cap 222 to a limit position. The limit position may be defined at a point on the arc of rotation furthest from its first end at which the outlet element 220 is still in the closed configuration. As the outlet element 220 is rotated from the limit position towards the second end of the arc of rotation the intake opening 223 will gradually move across a portion of the first seal 216 such that a flow path is defined from the valve opening 215 through the flow space 217 to the intake opening 223. As the outlet element 220 is rotated further from the first end of the arc of rotation, the area of the flow path may gradually increase until the outlet element 220 reaches a reaching a fully open position in which the valve opening 215 and the intake opening 223 are aligned. The fully open position may coincide with the second end of the arc of rotation. In the open configuration, at least a portion of the intake opening 223 is arranged between the valve opening 215 and the first seal 216.

When the outlet element 220 is in the open configuration at least a part of the intake opening 223 is arranged between the valve opening 215 and the first seal 216 in the liquid flow path through the outlet valve 202 such that at least a portion of the intake opening 223 is in liquid communication with the valve opening 215.

The relative axial positions of the axle 213 and the outlet element 220 may be fixed using retention features, for example in the form of an annular clip 226 provided between the cap 222 and the axle 213.

In a further aspect of the present disclosure, an outlet valve according to any aspect of the present disclosure may form part of an ostomy appliance further comprising an ostomy bag. The outlet valve may be attached to an outer face of a wall of the ostomy bag for draining liquid from a cavity of the ostomy bag. An ostomy bag aperture may be provided through the wall; the backing flange of the outlet valve being affixed or attached to the wall such that the ostomy bag aperture is in fluid communication with the hollow bore. The outlet valve may therefore be operated to open and close a fluid pat out of the cavity of the ostomy bag.

The outlet valve may be arranged adjacent to a lower edge or apex of the ostomy bag. The outlet valve may be oriented such that in the closed configuration the outlet element may substantially overlie the cavity of the ostomy bag and in the open configuration at least a portion of the outlet element extends across a lower edge of the cavity of the ostomy bag.

Whilst preferred aspects of the present disclosure have been described, these are by way of example only and non-limiting. It will be appreciated by those skilled in the art that many alternatives are possible within the ambit of the disclosure. For example, features described as part of one aspect may be combined with features of one or more other aspects unless the context clearly requires otherwise. Further, the following features may be applicable to any aspect of the disclosure.

As noted above, in this specification locations and orientations of features may be described with reference to the ostomy appliance being "in use", "orientated as it would be in use" or similar. Such terms refer to the intended orientation of the ostomy appliance when it is adhered to a body of an ostomate with the ostomate in a standing position.

Any outlet valve according to the present disclosure may be configured such that when attached to an outer face of an ostomy bag in use, the axis of rotation of the outlet element may be arranged generally perpendicular to the elongate axis of the outlet tube and perpendicular to a generally planar attachment face of the backing flange such that the axis is generally perpendicular to the body of the ostomate in use.

In use, the outlet tube may be arranged in a storage position at the first end of the arc of rotation, the outlet element being in the closed configuration. In this storage position, the outlet tube may be oriented such that the outlet end is arranged generally upwards and overlies the backing flange. In the storage position the outlet tube may overlie a cavity of the ostomy bag.

To drain liquid from an ostomy appliance comprising an outlet valve according to any aspect of the present disclosure, the user may grip the outlet element and rotate the outlet tube along an arc of rotation away from the first, upward end of the arc of rotation. A limit position of the outlet element may be defined at a point on the arc of rotation furthest from its first end at which the outlet element is still in the closed configuration.

The limit position may provide a convenient position for the user to pause rotation of the valve and to attach a drain appliance such as a night bag to the outlet tube before the outlet tube is moved into the open configuration, thereby limiting the possibility of spillage of the output liquid. The outlet tube may then be rotated further to increase an area of the flow path from the base opening to the intake opening, for example by increasing the alignment of the base and intake openings or by moving the intake opening past a seal, and thereby allow more fluid to flow out of the valve, and to orient the outlet tube downwards for convenient drainage into the night bag or to the exterior.

In use, when the valve opening and intake opening are at least partially aligned or otherwise at least partially in liquid communication the outlet element is in the open configuration. As the outlet tube is moved from its limit position towards the second end of the arc of rotation the apertures will become gradually more aligned or an area of the flow path between them will increase until reaching a fully open position in which both apertures are aligned. The fully open position may coincide with the second end of the arc of rotation.

After drainage of the ostomy bag, or when the user wishes to interrupt the flow of liquid out of the outlet valve, the user may rotate the outlet tube upwards to move the outlet element back into the closed configuration. If used, a night drainage bag or other appliance can be disconnected from the outlet tube once the outlet element is in the closed configuration, avoiding spillages.

In any aspect, retention features may be provided for retaining the axle inside the cap. For example, these may comprise cooperating protrusions and/or recesses. The retention features may also be configured to prevent relative axial motion between the cap and the axle during rotation.

In any aspect, the valve opening may define the only fluid path out of the hollow bore away from the ostomy bag.

In any aspect, the outlet element and/or the valve base may be provided with detents configured to prevent accidental opening and/or to provide audible and/or tactile feedback confirming the rotational position of the outlet element, and therefore whether the outlet element is in the open or closed configuration, to the user. For example, a detent may be arranged at or near the limit position to indicate the point at which the outlet element is about to move into the open configuration.

In any aspect, one or more of the seals may be in the form of an O-ring.

In any aspect, the backing flange and the axle may be formed integrally, for example being formed as a single moulding, or may be formed separately and subsequently assembled such that the axle is affixed to the backing flange. If formed separately, assembly may occur after attachment of the backing flange to an ostomy bag. This may facilitate assembly, as the height of the axle would not need to be accommodated by the assembly machinery (for example, a welding apparatus) during attachment of the backing flange to the ostomy bag.

In any aspect, at least a portion of the outlet tube may be formed integrally with the cap. Alternatively, the outlet tube may be formed separately and subsequently affixed to the cap.

In any aspect, the outlet tube may comprise a relatively rigid intake portion and a relatively flexible outlet portion. The relatively flexible outlet portion may be affixed to the relatively rigid intake portion in any suitable manner, for example by over-moulding the relatively flexible outlet portion onto the relatively rigid intake portion. The relatively flexible outlet portion may be resilient. The outlet valve according to any aspect of the disclosure may be configured for use with a relatively rigid connector, for example for connecting the outlet valve to a drainage bag or other appliance. The relatively rigid connector may have an outer diameter and the relatively flexible outlet portion of the outlet tube may have an outlet diameter marginally smaller than the connector outer diameter such that, on insertion of the connector into the relatively flexible outlet tube portion in use, the relatively flexible outlet tube portion may flex to accommodate the connector and thereby form an effective seal.

In any aspect, the valve opening may define the only fluid path out of the hollow bore away from the ostomy bag.

In any aspect, the seal(s) may be stationary (i.e. do not rotate) relative to the axle in use. One or more seals may be affixed to the axle.

A lubricant may be provided between the rotating components to ease rotation and improve sealing.

In any aspect of the present disclosure, the outlet element may be retained in an axial direction relative to the housing, such that there is no relative axial movement between the outlet element and the valve base during rotation.

Other features of the ostomy appliance, for example the shape and construction of the ostomy appliance inner and outer walls and comfort layer, may vary from those shown in the illustrated aspects. Similarly, the shape of the valve opening may vary from those shown in the illustrated aspects.

The outlet valve of the present disclosure is described herein as being suitable for an ostomy appliance comprising an ostomy bag. An outlet valve according to any aspect of the present disclosure may be suitable for use in other applications, for example a drainage bag or catheter collection bag.

The invention claimed is:

1. An outlet valve for an ostomy appliance comprising:
   an axle defining a hollow bore for receiving a liquid output from the ostomy appliance, the axle comprising a curved lateral wall; and
   an outlet element comprising a cap arranged concentrically with the axle and an outlet tube affixed to the cap;
   wherein a valve opening is defined in the curved lateral wall; and
   the cap is rotatable around the axle to move from a closed configuration in which the valve opening is not in liquid communication with the outlet tube to an open configuration in which the valve opening is in liquid communication with the outlet tube;
   wherein the outlet valve further comprises at least one seal configured to provide sealing between the cap and the axle around a circumference of the axle and sealing between the intake opening and the valve opening when the outlet element is in the closed configuration;
   wherein the at least one seal comprises a continuous first seal configured to provide sealing between the cap and the axle around a circumference of the axle and wherein the distance between the first seal and a basal end of the axle varies around the circumference of the axle.

2. The outlet valve as claimed in claim 1 wherein at a first circumferential position of the axle, the first seal is at a distance from the basal end that is less than or equal to a distance from the basal end to a proximal edge of the valve opening.

3. The outlet valve as claimed in claim 2, wherein at a second circumferential position of the axle, the first seal is at a distance from the basal end that is greater than or equal to a distance from the basal end to a distal edge of the valve opening.

4. The outlet valve as claimed in claim 3 wherein in the closed configuration the intake opening is arranged at the second circumferential position, such that the first seal is arranged between the intake opening and the valve opening.

5. The outlet valve as claimed in claim 1 further comprising an annular second seal arranged around a circumference of the axle.

6. The outlet valve as claimed in claim 5 wherein the annular second seal is arranged between the basal end of the axle and a proximal edge of the valve opening.

7. The outlet valve as claimed in claim 1 wherein the outlet tube comprises an intake opening, wherein the outlet tube is configured to rotate with the cap such that on rotation of the cap the intake opening of the outlet tube is moved between an open configuration in which the intake opening is in liquid communication with the valve opening and a closed configuration in which the intake opening is not in liquid connection with the valve opening, wherein in the open configuration at least a part of the intake opening is arranged between the valve opening and the first seal such that at least a portion of the intake opening is in liquid communication with the valve opening.

* * * * *